United States Patent [19]

Friese et al.

[11] Patent Number: 5,334,350

[45] Date of Patent: Aug. 2, 1994

[54] RESISTANCE PROBE FOR DETERMINING GAS COMPOSITIONS AND METHOD OF PRODUCING IT

[75] Inventors: Karl-Hermann Friese, Leonberg; Werner Gruenwald, Gerlingen; Hans-Martin Wiedenmann; Gerhard Hoetzel, both of Stuttgart, all of Fed. Rep. of Germany

[73] Assignee: Robert Bosch GmbH, Stuttgart, Fed. Rep. of Germany

[21] Appl. No.: 861,810

[22] PCT Filed: Nov. 24, 1990

[86] PCT No.: PCT/DE90/00909

§ 371 Date: Jun. 19, 1992

§ 102(e) Date: Jun. 19, 1992

[87] PCT Pub. No.: WO91/09301

PCT Pub. Date: Jun. 27, 1991

[51] Int. Cl.$^5$ .................. G01N 27/04; H01C 1/02; H01C 7/00
[52] U.S. Cl. ..................... 422/98; 422/88; 338/34; 338/229; 73/31.06
[58] Field of Search .......... 422/98, 94, 88, 83; 436/127, 137; 73/31.06, 31.05; 204/424–426, 428, 429; 338/34, 229, 221

[56] References Cited

U.S. PATENT DOCUMENTS

| | | | |
|---|---|---|---|
| 4,322,980 | 4/1982 | Suzuki et al. | 73/727 |
| 4,395,319 | 7/1983 | Torisu et al. | 204/429 |
| 4,457,161 | 7/1984 | Iwanaga et al. | 73/23 |
| 4,706,493 | 10/1987 | Chang et al. | 422/98 |
| 4,713,166 | 12/1987 | Kojima et al. | 204/429 |
| 4,776,943 | 10/1988 | Kitahara | 204/429 |
| 4,859,307 | 8/1989 | Nishizawa et al. | 204/429 |
| 4,883,947 | 11/1989 | Murase et al. | 338/34 |
| 4,904,291 | 2/1990 | Siebers et al. | 264/43 |
| 4,908,119 | 3/1990 | Saito et al. | 204/429 |
| 4,928,513 | 5/1990 | Sugihara et al. | 338/34 |
| 5,003,812 | 4/1991 | Yagawara et al. | 422/98 |
| 5,137,615 | 8/1992 | Friese et al. | 204/424 |
| 5,144,249 | 9/1992 | Kurishita et al. | 204/429 |
| 5,160,598 | 10/1992 | Sawada et al. | 204/429 |
| 5,164,068 | 10/1992 | Udo et al. | 204/429 |
| 5,169,512 | 12/1992 | Wiedenmann et al. | 204/424 |

*Primary Examiner*—Robert J. Warden
*Assistant Examiner*—T. A. Trembley
*Attorney, Agent, or Firm*—Spencer, Frank & Schneider

[57] ABSTRACT

A resistance probe is proposed for detecting gas compositions, particularly in the exhaust gases of internal combustion engines. This resistance probe has the advantage over prior art resistance probes that, with a short response time, it is considerably more aging resistant. This is accomplished in that the resistance layer configured as a semiconductor layer is introduced or sintered into recesses or slits provided for this purpose in the prefabricated sensor carrier body and above it is applied a porous, electrically non-conductive engobe or a protective layer structure in the form of a grid or raster. These measures enable the measuring gas to gain access to the semiconductor layer, but the semiconductor layer is simultaneously protected against corrosive, erosive and/or cavitative attacks from the exhaust gas.

25 Claims, 4 Drawing Sheets

RESISTANCE PROBE FOR DETERMINING GAS COMPOSITIONS AND METHOD OF PRODUCING IT

STATE OF THE ART

The invention is based on a generic resistance probe. Such resistance probes are known, for example, from German Patent 2,908,916, in which a heating conductor, electrodes, a semiconductor layer as well as a gas-permeable cover layer, separated by insulating layers, are applied in multi-layer technology onto a ceramic carrier plate. Experiments have shown that such protective layers do not exhibit satisfactory characteristics with respect to adhesion and reproducibility.

ADVANTAGES OF THE INVENTION

In contrast thereto, the resistance probe according to the invention comprises the following layers: an insulating ceramic substrate, a superposed pair of electrodes, a superposed semiconductor layer, a superposed ceramic covering, and at least one covering sheet disposed on the pair of electrodes and containing at least one recess in which the semiconductor layer with the ceramic covering is disposed on the pair of electrodes and which allows a gas mixture to pass through to the ceramic cover. The semiconductor layer functions as a gas sensor and is in electrical contact with the pair of electrodes. The ceramic covering is configured as an engobe protective layer with a plurality of pores which allow the gas mixture to pass through to the semiconductor layer.

A second embodiment of the invention comprises the following layers: an insulating ceramic substrate, a superposed pair of electrodes, a superposed semiconductor layer, and a superposed ceramic covering. The semiconductor layer functions as a gas sensor and is in electrical contact with the pair of electrodes. The ceramic covering is configured as a protective layer structure produced by thick-film technology in the form of a pattern of regions covering the semiconductor layer and with openings which allow access for the gas mixture to the semiconductor layer. The Invention has the advantage of its layer structure having sufficient stability under permanent stress. On the one hand, the structure according to the invention delays chemical aging of the resistance layer in that corrosion of the resistance layer, that is configured as a semiconductor layer, due to contaminants from the exhaust gas is prevented and, on the other hand, mechanical aging caused by abrasion of the resistance layer due to particles in the stream is also delayed. Even after long periods of operation, release of the semiconductor layer from the carrier is not observed.

Moreover, the application methods for the porous engobe protection layer, namely screen-printing, insertion of a porous sintering film or dripping in a suspension, are less expensive than the plasma spraying method employed in the past.

The method according to the invention is distinguished in that initially a sensor carrier body equipped with electrodes and an integrated heating element is prefabricated and sintered at high temperatures, whereupon a semiconductor layer is then applied as the resistance layer. This layer possibly carries an engobe protective layer and is sintered in together with the latter at lower temperatures. The advantage of this method is that the engobe protective layer is unable to react with the semiconductor layer during the sintering process as well as during later operation of the sensor and is therefore sufficiently stable.

Another advantageous method includes the application of a protective layer structure provided with openings only in certain regions so as to ensure access of the measuring gas to the semiconductor layer. The adhesion of the protective layer structure can be further improved by pressing it into the semiconductor layer before the sintering.

BRIEF DESCRIPTION OF THE DRAWING FIGURES

Two embodiments of the invention are illustrated in the drawings and will be discussed in greater detail in the description below.

DETAILED DESCRIPTION OF THE EMBODIMENTS

Unless otherwise mentioned, all layers of the resistance probe according to the invention are applied in a screen-printing process.

Figure 1:
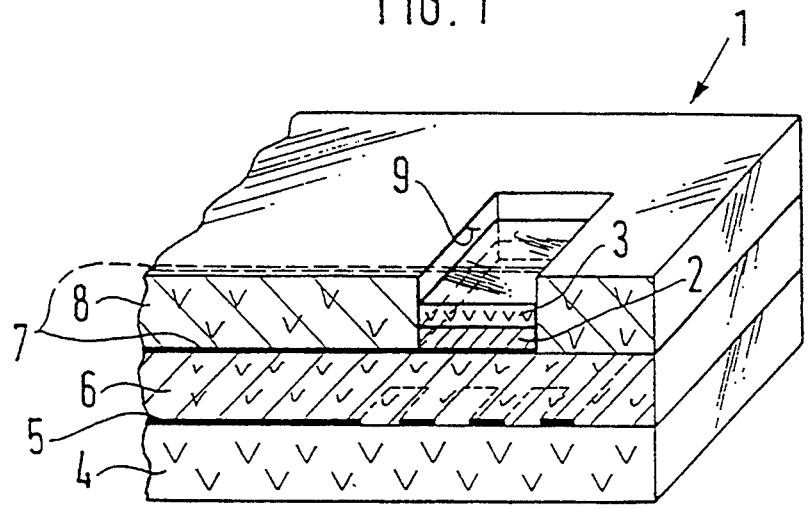
FIG. 1 depicts the structure of a resistance probe according to a first embodiment of the invention.

The sensor carrier body 1 of FIG. 1 is prefabricated in multi-layer technology from materials and according to process steps as disclosed in German Patent 2,908,916. For this purpose, a meander-shaped heating conductor 5 is applied to a thin film 4 of organic material and of an insulating ceramic material, preferably of aluminum oxide including more than 90 volume % $Al_2O_3$. On top of it are applied, separated by a second thin sheet 6, electrodes 7 and then at least one aluminum oxide containing ceramic cover layer 8. Cover layer 8 is provided with a recess or opening 9. The individual layers are dried intermediately if required and/or pre-sintered. The entire carrier body 1 is then sintered at a temperature of at least 1550° C.

The intermediate drying of carrier body 1 may also be omitted if the layer sequence has sufficient stability for the sintering process without being intermediately dried.

In a next process step, a semiconductor layer 2 in the form of a suspension or a screen-printing paste is introduced into the recess 9 provided for this purpose in cover layer 8. After intermediate drying of layer 2, if required, a porous engobe protective layer 3 is applied on top of it. Different methods are possible to accomplish this. Layer 3 may be produced, for example, by dripping in an engobe suspension, by printing on a screen-printing paste, or by inserting a thin, porous sintering sheet.

In the last process step, the resistance probe is sintered at 1150° to 1400° C.

According to a preferred embodiment, the sintered carrier body 1 may initially be supplied with a semiconductor layer 2 which is sintered in at 1150° to 1400° C. Only then is the engobe protective layer 3 applied and sintered in at 1150° to 1400° C.

In the sintered state, the engobe layer is composed of aluminum titanate or mixtures thereof with metal oxides. Applicable oxides are, for example, titanium dioxide, zirconium dioxide, yttrium stabilized zirconium dioxide, magnesium spinel or zirconium titanate. Mixtures of aluminum titanate and titanium dioxide preferably containing less than 50 volume percent titanium dioxide have been found to be particularly advantageous. The engobe composition according to the invention is selected in such a way that no undue reaction with semiconductor layer 2 takes place, neither during production nor during operation of the probe. For example, the aluminum titanate may be ATG made by Dynamit Nobel, which contains stabilizers in addition to aluminum oxide and titanium dioxide and which is composed, for example under the name "Aluminium Titanate ATG-3", in weight percent, of 53.8% $Al_2O_3$, 32.75% $TiO_2$, 3.0% $ZrO_2$, 7.9% $SiO_2$, 2.1% $MgO$. 0.2% $Fe_2O_3$, 0.2% $Na_2O$ and less than 0.05% $CaO$.

To improve the layer strength of the engobe according to the invention, the addition of small percentages of silicate containing fluxing agents has been found to be particularly advantageous, for example, in the form of $SiO_2$-$TiO_2$-$ZrO_2$ glass. The addition of the fluxing agents may also be effected in the form of metal-organic compounds such as, for example, alkoxides, propyl titanate, propyl zirconate, butyl titanate or butyl zirconate. It is preferable to use fluxing agents in the engobe layer which correspond to the fluxing agents of the ceramic substrate.

To ensure the gas access to the semiconductor layer the engobe must of necessity be porous. This is enhanced by the addition of pore formers, such as, for example, soot, theobromine, indanthrone or polywaxes, to the engobe suspension or paste.

Figure 2:
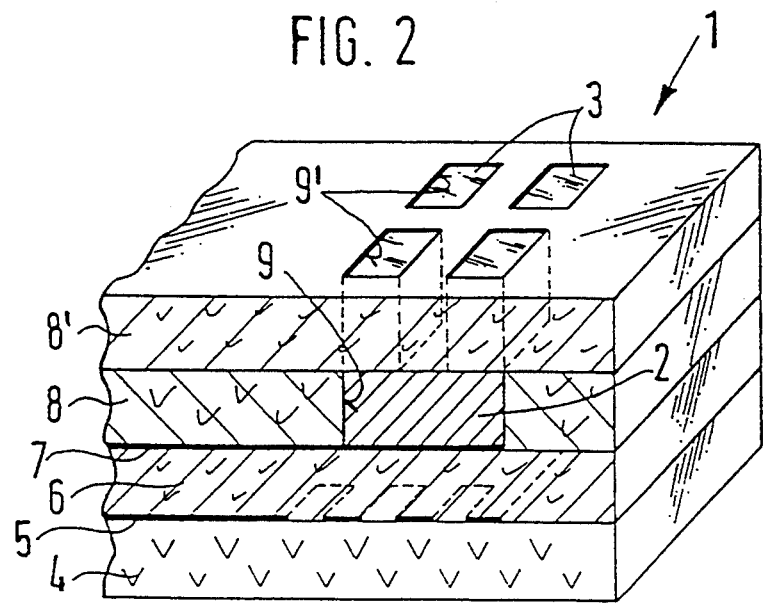
FIG. 2 depicts an alternative to the first embodiment.

FIG. 2 shows an alternative to the embodiment shown in FIG. 1, with the particularity that, to accommodate the semiconductor layer 2 and the engobe protective layer 3, respectively, cover layer 8 and 8', respectively, are provided with corresponding recesses. As can be seen in FIG. 1 and FIG. 2, cover layer 8 may be provided, for example, with a larger square recess 9 and cover layer 8' with several recesses 9' having a square cross section, all arranged above recess 9. Otherwise, this embodiment can be produced in the same manner as described in connection with FIG. 1.

In contrast to the embodiment shown in FIG. 1, the variation of FIG. 2 is provided, in an advantageous manner, with an improved mechanical strength thanks to the grid-shaped configuration of cover layer 8'.

Figure 3:
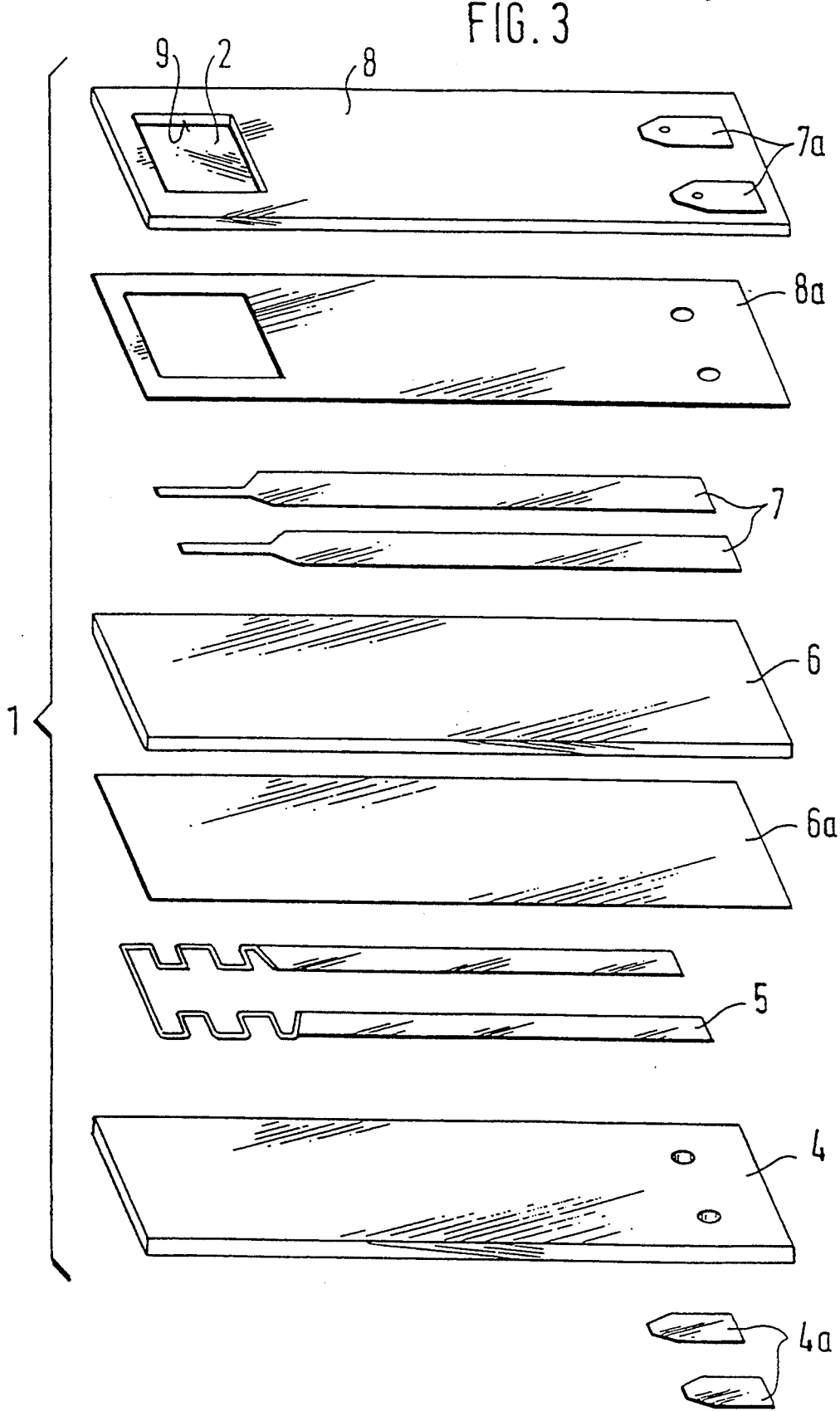
FIG. 3 depicts the layout of a resistance probe according to the invention.

FIG. 3 depicts a layout for a further embodiment of the resistance sensor according to the invention. An insulating substrate 4 is composed of an aluminum film provided with connecting holes, with the film containing 90% aluminum oxide and having a thickness of 0.5 mm. On its one large surface, the film is provided with platinum cermet contacts 4a and on the other large surface with a platinum cermet heating conductor 5. This is followed by a screen-printed layer of an interlaminary binder 6a composed of 90% aluminum oxide. On a separating sheet 6 having a thickness of 0.5 mm, electrodes 7 are applied which are composed of 90% platinum cermet. The leads to electrodes 7 are covered with a further layer of an interlaminary binder 8a composed of 90% aluminum oxide and one or two covering films which have a thickness of 0.5 mm and are composed of 90% aluminum oxide are applied or glued on top of the binder. Covering layer 8 is provided with a recess 9 and with contacts 7a as well as contacting holes for electrodes 7.

The sensor carrier body prefabricated in this way is sintered at temperatures between 1500° and 1650° C. and then semiconductor layer 2 and possibly the engobe protective layer 3 are introduced into the recess 9 provided for this purpose in cover layer 8 and are sintered in at temperatures between 1150° and 1400° C., preferably at 1200° to 1300° C.

Figure 4:
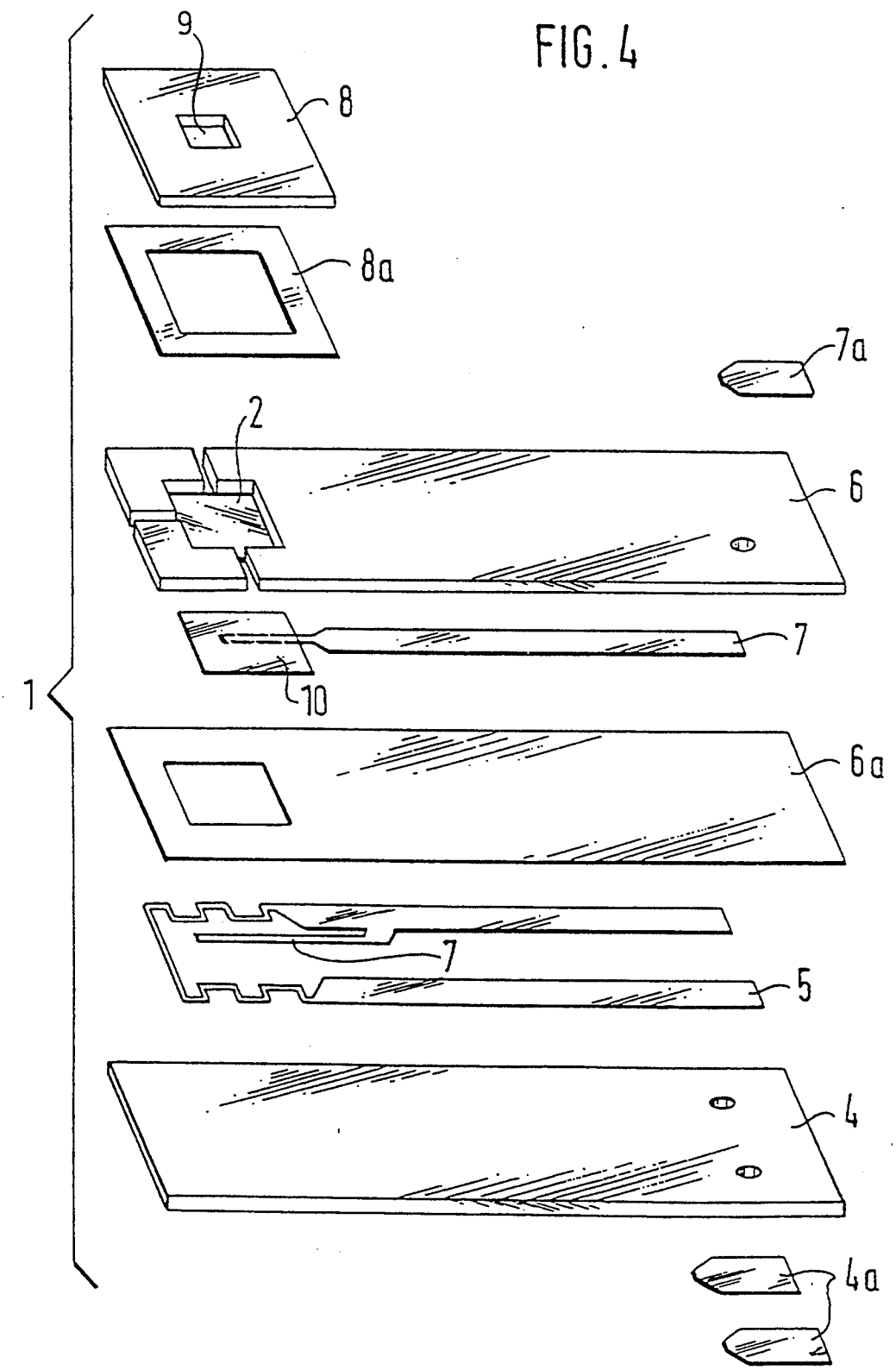
FIG. 4 depicts the layout of a further embodiment.

FIG. 4 depicts a preferred embodiment of the resistance probe of FIG. 3. According to this embodiment, an intermediate film 6 is provided with a recess and with slits which are configured in such a way that semiconductor layer 2 is substantially protected against corrosive, erosive and/or cavitative attacks from the exhaust gas. The recess may be lined with a layer 10 of a cavity forming agent such as, for example, theobromine. The semiconductor layer 2 can be introduced into the prefabricated sensor carrier body 1 of FIG. 4 according to various methods: by dripping in a suspension, producing a suction effect from capillary forces, with the substrate surface being pretreated, if required, for example, by cleaning with alcohol or by inserting a porous, sintering titanium dioxide sheet. By means of an interlaminary binder 8a, a covering layer 8 is applied to intermediate film 6 and is provided with a recess 9. Electrodes 7 are connected with contacts 7a and 4a, respectively, by way of contacting holes. One of electrodes 7 may be short-circuited with heating element 5.

Figure 5A:
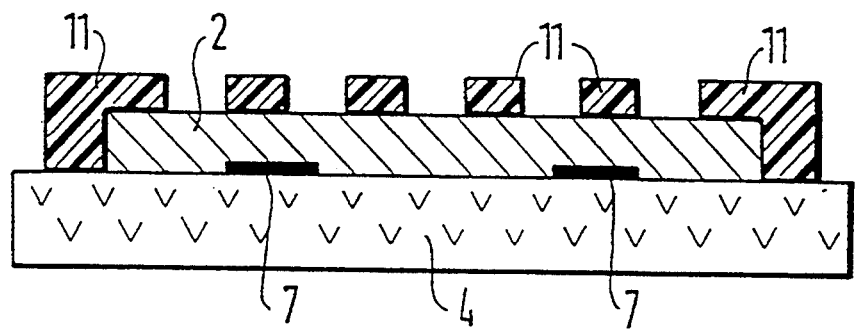
FIGS. 5A and 5B depict the production of a preferred embodiment.

FIG. 5A is a sectional view of a further embodiment of a resistance probe according to the invention. Electrodes 7, semiconductor layer 2 as well as the protective layer structure 11 equipped with regions covering semiconductor layer 2 and openings ensuring free access for the measuring gas to semiconductor layer 2 are applied to the insulating substrate 4.

Figure 5B:
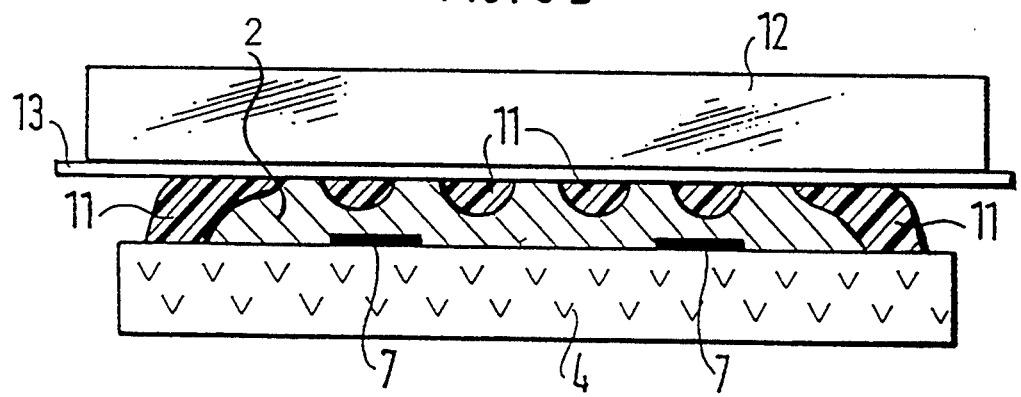

However, the properties of such a probe, particularly its resistance to aging, can be further improved if, as shown in FIG. 5B, the protective layer structure 11 applied to semiconductor layer 2 is fitted into the semiconductor layer 2 before the sintering process, for example by means of a pressing die 12 while employing a separating sheet 13, for example, a siliconized polyester sheet. Pressures of, for example, 20 to 80 bar and advantageously temperatures from room temperature up to the drying temperature of the printed layers can be employed in this case.

Figure 6:
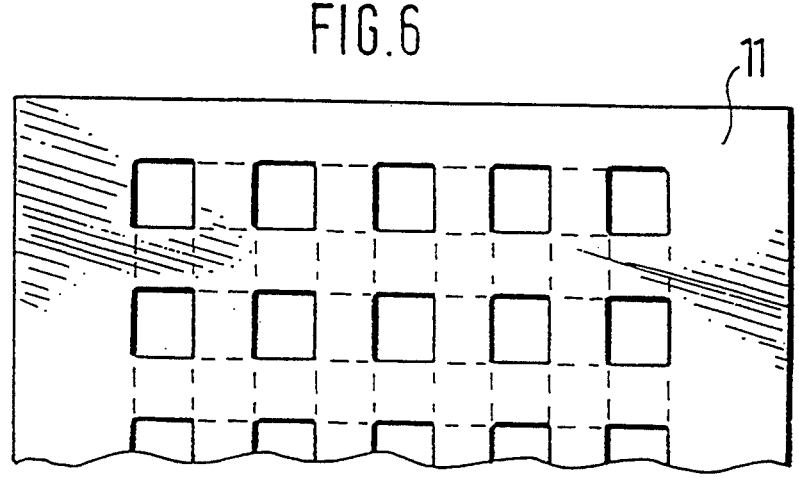
FIG. 6 depicts an advantageous protective layer structure.

FIG. 6 depicts a grid and raster-shaped protective layer structure before it is pressed in.

Aside from the protective layer structure shown in FIG. 6, the most varied other structures are also possible; that is, the openings which give the measuring gas direct access to the semiconductor layer 2 may also be composed, for example, of slits or round or oval openings.

The operation of the resistance probe according to the invention will now be described for the example of a titanium dioxide sensor. It is based on the chemical equilibrium between lattice defects in the titanium dioxide and gaseous oxygen in the surrounding atmosphere. A low oxygen concentration in the atmosphere as, for example, in the case of a fatty mixture or in a vacuum, due to the great difference in oxygen activity between the titanium dioxide and the atmosphere, causes the transfer of the oxygen ions from the titanium dioxide into the atmosphere. Oxygen-caused lattice defects and free electrons are created within the titanium dioxide. Thus, due to the development of free electrons, the resistance of the sensor drops in the fatty region. In the lean region, the opposite reaction takes place, and the resistance of the sensor increases.

Generally, the following equation applies:

$$R_t = A \cdot \exp\left(\frac{E}{kT}\right) \cdot (PO_2)^{\frac{1}{n}}$$

where A is a constant, E is the activation energy for the formation of the lattice defect, k is the Bolzmann constant and n a constant which is a function of the nature of the lattice defects. In the temperature range of the oxygen concentration measurement, the value of n is approximately 4 and is based on the conductivity over $Ti^{3+}$ locations.

This equation shows that, with a constant ambient temperature, the resistance of the sensor is an exclusive function of the oxygen concentration. However, no chemical or mechanical change in the semiconductor layer must take place which would cause a change in resistance.

EXAMPLE

To produce a resistance probe according to the invention, a carrier made of a pre-sintered $Al_2O_3$ film of a thickness of 0.5 mm was imprinted in a screen-printing process with initially two platinum electrodes. For this purpose, a conventional Pt cermet paste composed of 85 parts per weight Pt powder and 15 parts per weight YSZ powder was employed.

After printing on the electrodes, the structure was laminated and sintered at 1500°–1550° C. A semiconductor layer based on a pasty preparation with $TiO_2$ of an average grain size of about 0.5 μm was printed onto this prefabricated sensor carrier body.

Then the protective layer structure in the form of a grid or raster as shown in FIG. 2 was printed onto the semiconductor layer. A pasty preparation of the following composition was employed: 70 volume % $Al_2O_3 \cdot TiO_2$, average grain diameter 2.5 μm, 30 volume % $TiO_2$, as above, and a catalytically active additive of 1 weight % Pt powder, specific surface area 15 m²/g according to German Patent 2,265,309.

Seventy percent of the surface area of the semiconductor layer were covered with the pasty preparation. The edge length of the practically square opening was 0.1 to 0.2 mm.

The still damp protective layer structure was then pressed into the semiconductor layer by means of a pressing die.

Following the pressing process, the material was sintered for three hours at a temperature in the range from 1250° to 1300° C. The resistance probe obtained in this way was inserted into a housing of the type disclosed in DE-OS [German unexamined published patent application] 3,206,903 and employed to control the air/fuel ratio in an internal combustion engine.

We claim:

1. A resistance probe to determine the oxygen content in gas mixtures, the resistance probe including a sensor carrier body comprising the following superposed layers:
    an insulating ceramic substrate;
    an electrode layer including a pair of electrodes;
    a semiconductor layer, which is capable of functioning as a gas sensor, and which is in electrical contact with said pair of electrodes;
    at least one covering sheet disposed on said pair of electrodes and containing at least one recess in which said semiconductor layer is disposed on said pair of electrodes and which allows a gas mixture to pass through to said semiconductor layer; and
    a ceramic covering disposed in said at least one recess and on, and completely covering, the semiconductor layer, with the ceramic covering being a porous engobe protective layer.

2. A resistance probe according to claim 1, wherein the porous engobe protective layer contains as its inorganic components one of aluminum titanate and mixtures of aluminum titanate with at least one of titanium dioxide, zirconium dioxide, yttrium stabilized zirconium dioxide, magnesium spinel, and zirconium titanate.

3. A resistance probe according to claim 2, wherein said porous engobe protective layer contains as its inorganic components a mixture of aluminum titanate with less than 50 volume percent titanium dioxide.

4. A resistance probe according to claim 1, wherein the porous engobe protective layer contains as its inorganic components at least one of the following stabilizer additives: zirconium dioxide, silicon dioxide, magnesium oxide, iron oxide, sodium oxide, and calcium oxide.

5. A resistance probe according to claim 1, wherein the porous engobe protective layer as its inorganic components, fluxing agent phases.

6. A method for the production of a resistance probe according to claim 1, said method comprising the steps of:
    forming a layer system by the layer-by-layer application of said pair of electrodes, and said at least one covering sheet onto said insulating ceramic substrate;
    sintering at a first sintering temperature the thus obtained layer system to form a prefabricated sensor carrier body; and attaching said semiconductor layer and said engobe protective layer to said layer system by introducing a semiconductor material to form said semiconductor layer and an engobe material to form said engobe protective layer into said at least one recess provided for this purpose in the at least one covering sheet and by sintering the semiconductor material and the engobe material at a temperature lower than the first sintering temperature.

7. A method according to claim 6, wherein said step of attaching includes introducing at least one: a soot, theobromine, indanthrone, and polywaxes into said engobe material prior to sintering at the lower temperature to enhance production of pores.

8. A method according to claim 6, wherein the semiconductor material is introduced into the prefabricated sensor carrier body by at least one of capillary suction and suction through a plurality of lateral ventilation openings.

9. A method according to claim 6, wherein the at least one recess provided to accommodate the semiconductor layer when the prefabricated sensor carrier body is finished, is substantially filled with a cavity forming agent before the sintering at the lower temperature.

10. A method according to claim 6, wherein at least one of the semiconductor material and the engobe material is introduced into said at least one recess in the at least one covering sheet by dripping in a suspension of the respective material.

11. A method according to claim 6, wherein at least one of the semiconductor material and the engobe material is introduced into said at least one recess in the at least one covering sheet in the form of screen-printing pastes.

12. A method according to claim 6, wherein at least one of the semiconductor material and the engobe material is introduced into said at least one recess in the at least one covering sheet in the form of porous sintering films.

13. A method for the production of a resistance probe according to claim 6, wherein the step of attaching comprises the steps of:
  introducing the semiconductor material into said at least one recess in the at least one covering sheet;
  sintering the semiconductor material at a lower temperature than the sintering temperature of the layer system;
  introducing the ceramic covering material into said at least one recess in the at least one covering sheet; and
  sintering the ceramic covering material at a further lower temperature than the sintering temperature of the layer system.

14. A method for the production of a resistance probe according to claim 6, wherein said step of attaching comprises the steps of:
  introducing the semiconductor material and the ceramic covering material respectively, into at least one recess in the at least one covering sheet; and
  sintering the semiconductor material and the ceramic covering material at a lower temperature than the sintering temperature of the layer system.

15. A resistance probe according to claim 1, further comprising a heating element disposed on said insulating ceramic substrate and at least one intermediate film disposed between said heating element and said pair of electrodes.

16. A resistance probe to determine the oxygen content in gas mixtures, the resistance probe including a sensor carrier body comprising the following superposed layers:
  an insulating ceramic substrate;
  a pair of electrodes;
  a semiconductor layer, which is capable of functioning as a gas sensor, and which is in electrical contact with said pair of electrodes; and
  a ceramic covering disposed on said semiconductor layer and configured as a protective layer structure produced by thick-film technology and in the form of a pattern of regions which cover the semiconductor layer and of openings which allow access for a gas mixture to the semiconductor layer.

17. A resistance probe according to claim 16, wherein said protective layer structure has a pattern of one of a grid and a raster.

18. A resistance probe according to claim 16, wherein the protective layer structure includes at least one of aluminum titanate, zirconium titanate, sinter active titanium dioxide, magnesium spinel, aluminum oxide and mixtures of these substances.

19. A method for the production of a resistance probe according to claim 16, said method comprising the steps of:
  forming a prefabricated sensor carrier body by applying said pair of electrodes onto said insulating ceramic substrate, by laminating the layers together and by sintering at a first temperature;
  applying the semiconductor layer to said prefabricated sensor carrier body and sintering the prefabricated sensor carrier body at a temperature, which is lower than the first temperature; and
  applying the protective layer structure onto the semiconductor layer in the form of a pattern of said ceramic covering that cover the semiconductor layer and said openings which ensure access for the gas mixture to the semiconductor layer and sintering the protective layer structure at a temperature, which is lower than the first temperature.

20. A method according to claim 19, further comprising a further step of pressing the protective layer structure into the semiconductor layer.

21. A method according claim 19, wherein the temperature for sintering the prefabricated sensor carrier body is different than the temperature for sintering the protective layer structure.

22. A resistance probe for determining the oxygen content in gas mixtures, said resistance probe comprising:
  a layered sensor carrier body including superposed layers of an insulating ceramic substrate, a pair of laterally spaced electrodes, and at least one covering layer which is provided with at least one recess disposed above said pair of laterally spaced electrodes;
  a semiconductor layer disposed within said at least one recess and electrically contacting said pair of laterally spaced electrodes; and
  a ceramic cover having at least one opening and covering the semiconductor layer on the side of the semiconductor layer which is exposed a gas mixture.

23. A resistance probe according to claim 22, wherein said ceramic cover is part of said at least one covering layer; and said at least one opening comprises a plurality of recesses in said ceramic cover to form a protective layer structure.

24. A resistance probe according to claim 22, wherein said ceramic cover is an engobe protective layer and said at least one opening is a plurality of pores in said engobe protective layer.

25. A resistance probe according to claim 22, wherein said at least one covering layer further comprises a further covering layer having a plurality of secondary recesses disposed above said at least one recess of said at least one covering layer, and wherein said ceramic cover is a plurality of engobe protective layers, each disposed within a respective secondary recess, and said at least one opening is a plurality of pores in said plurality of engobe protective layers.

* * * * *

UNITED STATES PATENT AND TRADEMARK OFFICE
CERTIFICATE OF CORRECTION

PATENT NO. : 5,334,350
DATED : August 2, 1994
INVENTOR(S) : Karl-Hermann FRIESE et al.

It is certified that error appears in the above-indentified patent and that said Letters Patent is hereby corrected as shown below:

On the title page: Item

--[30] Foreign Application Priority Data

Dec. 19, 1989 [DE] Fed. Rep. of Germany . . . . . . . . . . . . . . . . 3941837--

Signed and Sealed this

Twenty-seventh Day of September, 1994

Attest:

BRUCE LEHMAN

*Attesting Officer*  *Commissioner of Patents and Trademarks*